US005827502A

United States Patent [19]
Klaveness et al.

[11] Patent Number: 5,827,502
[45] Date of Patent: *Oct. 27, 1998

[54] MICROPARTICULATE MICROBUBBLE-GENERATING CONTRAST AGENTS

[75] Inventors: Jo Klaveness, Oslo; Pal Rongved, Hellvik, both of Norway; Lars Stubberud, Sodertalje, Sweden

[73] Assignee: Nycomed Imaging AS, Oslo, Norway

[ * ] Notice: The term of this patent shall not extend beyond the expiration date of Pat. No. 5,558,856.

[21] Appl. No.: 478,037

[22] Filed: Jun. 7, 1995

Related U.S. Application Data

[62] Division of Ser. No. 256,149, filed as PCT/EP93/00027 Jan. 8, 1993, Pat. No. 5,558,856.

[30] Foreign Application Priority Data

Jan. 9, 1992 [GB] United Kingdom .................... 9200388

[51] Int. Cl.$^6$ ............................ A61K 49/04; A61B 5/055
[52] U.S. Cl. ........................ 424/9.52; 424/9.51; 424/9.37
[58] Field of Search ..................... 424/9.52, 9.5, 424/9.51, 450, 9.1, 937; 128/662.02

[56] References Cited

U.S. PATENT DOCUMENTS

| | | | |
|---|---|---|---|
| 5,141,738 | 8/1992 | Rasor et al. | 424/9.5 |
| 5,393,524 | 2/1995 | Quay | 424/9 |
| 5,531,980 | 7/1996 | Schneider et al. | 424/9.52 |
| 5,558,856 | 9/1996 | Klaveness et al. | 424/9.37 |

FOREIGN PATENT DOCUMENTS

WO 93/17212 10/1992 WIPO .
WO 93/00930 1/1993 WIPO .

*Primary Examiner*—Gary E. Hollinden
*Assistant Examiner*—Michael G. Hartley
*Attorney, Agent, or Firm*—Bacon & Thomas

[57] ABSTRACT

The present invention relates to contrast agents comprising microbubble-generating carbohydrate particles having a surfactant admixed within the microparticulate structure, wherein the microbubbles generated by the microparticles comprise a biocompatible low molecular weight fluorinated hydrocarbon. The contrast agents exhibit useful levels of contrast efficiency and/or stability and may be used in diagnostic applications such as ultrasound and MR imaging.

38 Claims, 1 Drawing Sheet

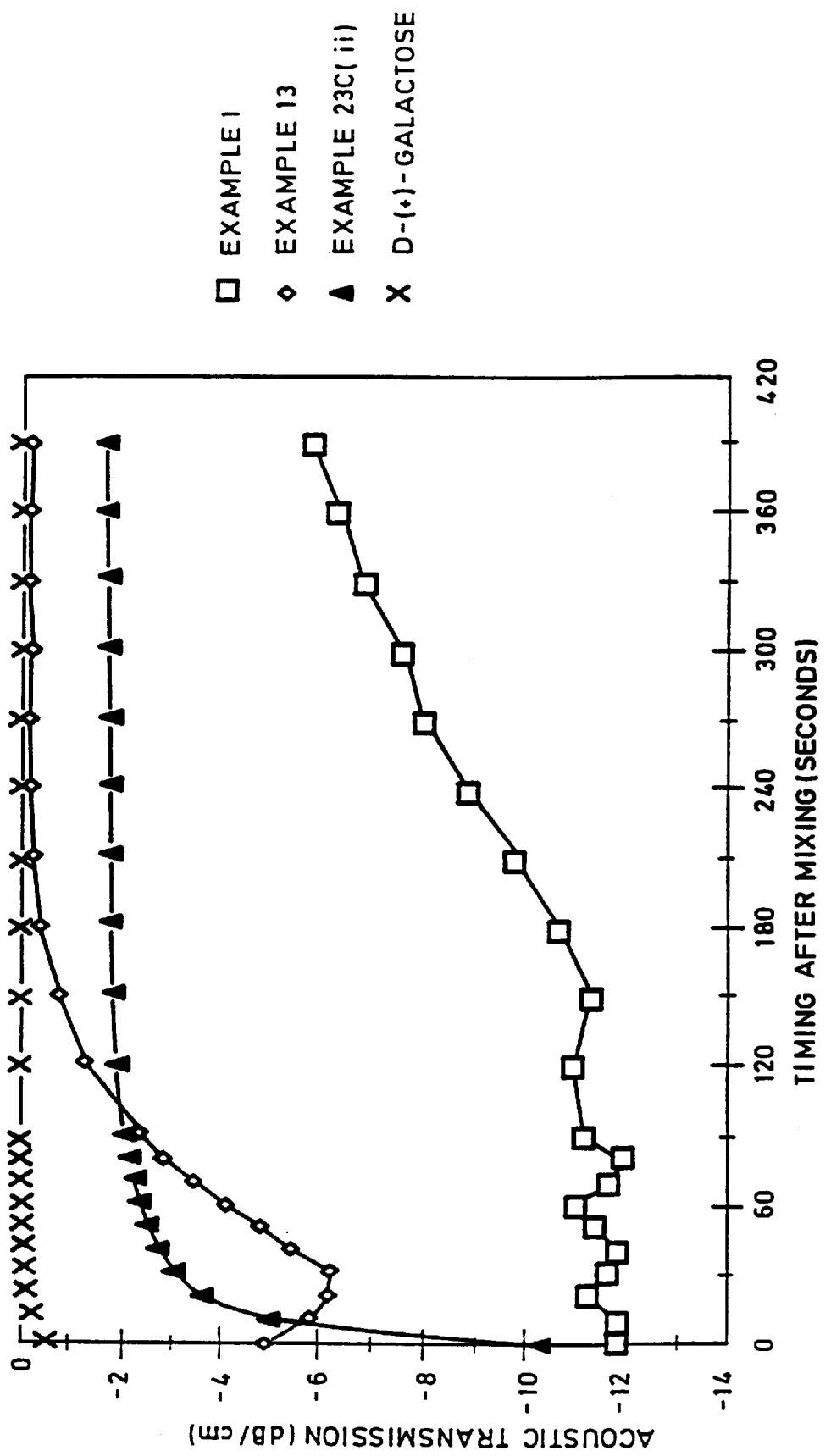

MICROPARTICULATE MICROBUBBLE-GENERATING CONTRAST AGENTS

This application is a Division of application Ser. No. 08/256,149, filed Dec. 9, 1994, U.S. Pat. No. 5,558,856, which is a 371 of PCT/EP93/00027, filed Jan. 8, 1993.

This invention relates to novel contrast agents, more particularly to new microparticulate contrast agents of use in diagnostic imaging.

It is well known that ultrasonic imaging comprises a potentially valuable diagnostic tool, for example in studies of the vascular system, particularly in cardiography, and of tissue microvasculature. A variety of contrast agents has been proposed to enhance the acoustic images so obtained, including suspensions of solid particles, emulsified liquid droplets, gas microbubbles and encapsulated gases or liquids. It is generally accepted that low density contrast agents which are easily compressible are particularly efficient in terms of the acoustic backscatter they generate, and considerable interest has therefore been shown in the preparation of gas-containing and gas-generating systems.

Initial studies involving free gas microbubbles generated in vivo by intracardiac injection of physiologically acceptable substances have demonstrated the potential efficiency of such bubbles as contrast agents in echocardiography; such techniques are severely limited in practice, however, by the short lifetime of the free bubbles. Interest has accordingly been shown in methods of generating and/or stabilising gas microbubbles for echocardiography and other ultrasonic studies, for example using emulsifiers, oils, thickeners or sugars.

Techniques involving the use of sugars in ultrasound contrast agents are described in, for example, U.S. Pat. No. 4,681,119, U.S. Pat. No. 4,442,843 and U.S. Pat. No. 4,657,756, which disclose the use of particulate solids having a plurality of gas-filled voids and preferably also a plurality of nuclei for microbubble formation. EP-A-0123235 and EP-A-0122624 suggest ultrasound contrast agents consisting of surfactant-coated or surfactant-containing gas-containing microparticles which may include a variety of sugars. Where surfactant-containing microparticles are described, these are prepared simply by commingling the surfactant with the microparticulate materials, e.g. by trituration.

DE-A-3834705 proposes the use of suspensions containing microparticles of mixtures of at least one $C_{10-20}$ fatty acid with at least one non-surface active substance, including sugars such as cyclodextrins, monosaccharides, disaccharides or trisaccharides, as well as other polyols and inorganic and organic salts; in practice only the use of galactose as the non-surface active material and only the use of saturated fatty acids are exemplified. The microparticulate materials are typically prepared by coprecipitating the fatty acid and non-surface active substance and comminuting the resulting product, e.g. using an air-jet mill.

One material of the type described in DE-A-3834705, SHU 508 (Levovist®), is described in the following publications:

Schlief, R. et al., Circulation Supplement III (1990) 82, p. 28; Schartl, M. et al., Circulation Supplement III (1990) 82, p. 261; Fritzsch, T. et al., Invest. Radiol. (1990) 25 (Suppl), pp. 160–161; Schlief, R. et al., Echocardiography (1990) 7, pp. 61–64; Loughery, E. J. et al., Echocardiography (1990) 7, pp. 279–292; and Smith, M. D. et al., JACC (1989) 13, pp. 1622–1628.

Gas-containing contrast media are also known to be effective in magnetic resonance (MR) imaging, e.g. as susceptibility contrast agents which will act to reduce MR signal intensity. Oxygen-containing contrast media also represent potentially useful paramagnetic MR contrast agents.

Furthermore, in the field of X-ray imaging it has been observed that gases such as carbon dioxide may be used as negative oral contrast agents.

A general disadvantage of most of the existing gas-containing/gas-generating particulate contrast agents such as the sugar-based agents discussed above is their relative lack of stability in vivo. This is a particular problem in applications such as echocardiography, where there is a need for improved contrast agents combining sufficient stability and small microbubble size (typically less than about 10 μm, preferably less than about 7 μm) to permit passage through the pulmonary capillary bed and so allow enhanced visualisation of the left side of the heart, preferably for more than one passage of circulation. There is accordingly a need for contrast agents which generate microbubble systems exhibiting good stability while still providing an effective level of contrast efficiency.

The present invention is based on our finding that contrast agents comprising microparticles of a carbohydrate having a surfactant admixed therewith (but excluding the previously disclosed mixtures of galactose and saturated $C_{10-20}$ fatty acids) may be used to generate microbubble systems exhibiting enhanced contrast effect and/or stability relative to previously proposed carbohydrate-based contrast agents. In the ultrasound field this may be demonstrated by, for example, in vitro measurements of initial attenuation levels and the half lives of the attenuative effect; a useful indication of the combined effect of these properties is the integral obtained by determining the area under the curve of a plot of attenuation against time.

BRIEF DESCRIPTION OF THE DRAWINGS

FIG. 1 shows the results for representative exemplified products and comparative results for unmodified milled D-(+)-galactose.

The term "surfactant" as used herein means any compound having amphiphilic properties capable of modifying surface tension.

Thus, according to one aspect of the present invention, Here are provided contrast agents comprising microbubble-generating carbohydrate microparticles having a surfactant admixed within the microparticulate structure, with the proviso that the surfactant is not a saturated $C_{10-20}$ fatty acid when the microparticulate carbohydrate is galactose.

The microparticulate carbohydrate is preferably water soluble, and subject to the foregoing proviso may for example be selected from hexoses such as glucose, fructose or galactose; disaccharides such as sucrose, lactose or maltose; pentoses such as arabinose, xylose or ribose; and polysaccharides such as α-, β- and γ-cyclodextrins, maltodextrin and glycogen; the term "carbohydrate" as used herein is also intended to embrace sugar alcohols, e.g. alditols such as mannitol or sorbitol. Microparticles of the above carbohydrates will normally have gas present as an inclusion in the voids of their crystal structure and/or adhered to their surface, which gas may generate microbubbles when, for example, the microparticles are suspended or dissolved in an injectable carrier liquid, for example water for injection, an aqueous solution of one or more inorganic salts (e.g. physiological saline or a physiological buffer solution), an aqueous solution of a monosaccharide (e.g. glucose or galactose) or disaccharide (e.g. lactose), or an aqueous solution of a physiologically tolerable monohydric or polyhydric alcohol (e.g. ethanol, propanol, isopropanol, ethylene glycol, propylene glycol, glycerine or polyethylene glycol).

In addition to or alternatively to air, any biocompatible gas may be employed in the contrast agents of the invention, for example nitrogen, oxygen, hydrogen, nitrous oxide, carbon dioxide, helium, argon, sulphur hexafluoride and low molecular weight optionally fluorinated hydrocarbons such as methane, acetylene or carbon tetrafluoride. The term "gas" as used herein includes any substance in the gaseous form at 37° C. The gas may be contained in the contrast agent in such a way that before use the product is non-contrast giving but becomes effective on administration, e.g. as a result of the gas forming microbubbles as a soluble carbohydrate matrix dissolves.

Additionally or alternatively the carbohydrate may incorporate one or more gas precursors, including carbonates and bicarbonates (e.g. sodium or ammonium bicarbonate) and aminomalonate esters.

Subject to the foregoing proviso a wide variety of surfactants may be used in the ultrasound contrast agents of the invention; it will of course be appreciated that the surfactant is required to be biocompatible, i.e. that it should be physiologically tolerable in the quantities in which it is to be administered. The surfactant is advantageously biodegradable in vivo or otherwise readily eliminable from the system.

The surfactant may, for example, be an amphiphilic lipid, e.g. selected from fatty acids and salts (e.g. alkali metal salts) thereof, steroid acids, sterols, phospholipids and glycolipids. Such lipids include high molecular weight (e.g. $C_{10-50}$) straight chain saturated and unsaturated aliphatic acids, such as capric, palmitic, hexadecanedioic, stearic, linolenic, behenic, docosanedioic and melissic acids; aralkanoic acids, e.g. phenyl lower alkanoic acids such as 2-phenylbutyric acid; salts of any of the foregoing acids; mono- and diglycerides, for example glyceryl esters of high molecular weight (e.g. $C_{10-50}$) aliphatic acids, such as glyceryl monolaurate; cholanic acids such as 5β-cholanic acid; cholesterol; sorbitan esters of fatty acids such as Span-type materials; high molecular weight (e.g. $C_{10-50}$) straight chain aliphatic alcohols such as stearyl alcohol and cetyl alcohol; phospholipids such as phosphatidyl choline (lecithin) and dioleoylphosphatidyl ethanolamine (DOPE); and mixtures thereof.

Other surfactants which may be employed include anionic surfactants, for example alkali metal alkyl sulphates such as sodium lauryl sulphate and sulphonated esters such as sodium dioctyl sulphosuccinate (docusate); and non-ionic surfactants, for example polyoxyethylene-polyoxyproplyene copolymers (e.g. poloxamers such as Pluronic F68) and polyoxyethylated sorbitan esters (e.g. polysorbates such as Tween-type materials).

The surfactant moiety may if desired be covalently linked to a substrate such as a carbohydrate prior to its admixture with the principal microparticulate carbohydrate. Thus, for example, a fatty acid such as palmitic acid (preferably in the form of a reactive derivative such as a corresponding acyl halide) may be used to esterify a (preferably appropriately O-protected) sugar such as galactose and the resulting lipophilically modified carbohydrate used as the surfactant in accordance with the invention.

The surfactant may, for example, be present in an amount of 0.01–5.0 wt. %, preferably 0.1–2.0 wt. %, relative to the microparticulate carbohydrate.

The contrast agents of the invention may be used in a variety of diagnostic imaging techniques, including ultrasound, MR and X-ray imaging. Their uses in diagnostic ultrasonic imaging and MR imaging, e.g. as susceptibility contrast agents, constitute preferred features of the invention.

The contrast agents of the invention may be prepared by any convenient method which leads to physical admixture of the surfactant within the microparticulate structure of the carbohydrate and to production of microparticles of the desired size.

In one preferred method according to the invention the carbohydrate and the surfactant are each dissolved in appropriate mutually miscible solvents (e.g. water in the case of the carbohydrate and a lower alkanol such as ethanol in the case of lipid surfactants such as fatty acids), the resulting solutions are mixed, the solvents are removed (e.g. by evaporation under reduced pressure), and the resulting solid mixture is micronised to yield the desired microparticles. It will be appreciated that all such operations should be effected under sterile conditions.

In an alternative method according to the invention a (preferably aqueous) solution of the carbohydrate is mixed with a liposome-forming material (e.g. a thin film of a lipid such as lecithin formed on the inner surface of the mixing vessel by evaporating the solvent from a solution of the lipid in an appropriate organic solvent, for example a chlorinated hydrocarbon such as chloroform) so as to form a liposome-containing carbohydrate solution from which the solvent may be removed (e.g. by freeze-drying) to yield a product comprising carbohydrate-containing liposomes; this product may be micronised to given microparticles of the desired size.

In general conventional micronisation techniques such as grinding or milling may be employed in processes according to the invention. Ball-milling of the solid mixture has been found to be particularly advantageous, permitting the preparation of microparticles in the form of aggregates (for example having an aggregate size of 20–125 micrometers, such as 30–50 micrometers) of particles having a particle size of, for example, 1–50 micrometers, such as 1–10 micrometers. Such aggregates will tend to contain a substantial volume of air adsorbed on their surfaces and entrained in voids such as interparticle cavities or at grain boundaries between the crystallites. The particle size may, for example, be selected to be substantially commensurate with the desired microbubble size. In ultrasonic applications such as echocardiography, in order to permit free passage through the pulmonary system and to achieve resonance with the preferred imaging frequencies of about 0.1–15 MHz, it may be convenient to employ microbubbles and microparticles having an average size of 0.1–10 $\mu$m, e.g. 1–7 $\mu$m; the use of microparticles of average size 1–4 $\mu$m to generate microbubbles with an average size of 4–7 $\mu$m is generally advantageous.

Substantially larger bubbles and particles, e.g. with average sizes up to 500 $\mu$m, may however be useful in other applications, for example gastrointestinal imaging.

Ultrasound contrast agents in the form of microparticles comprising a microbubble-generating carbohydrate in admixture with an amphiphilic organic acid containing in excess of 20 carbon atoms are the subject matter of our international patent application cofiled herewith and claiming priority from British patent application No. 9200387.0.

The following non-limitative Examples serve to illustrate the invention:

EXAMPLES 1–18

General Procedure

D-(+)-galactose (10.0 g) was dissolved in distilled water (14.2 g) at 50° C., sterile filtered and cooled on ice to a temperature of 4°–8° C. The stated amounts of the surfactants (in % w/w relative to the galactose) listed in Table I were each dissolved in the amount of 96% ethanol (or water in Examples 5 and 6) shown in the Table, at 50°–78° C., and the resulting solution was sterile filtered and then aseptically added to the cold aqueous galactose solution under stirring. The resulting mixture was evaporated to dryness under reduced pressure (10 torr, 40° C.), and the resulting solid product was dried in a desiccator overnight and then ground for 10 minutes under aseptic conditions in a stainless steel ball mill having a 50 ml grinding cup and 3×20 mm balls (Retsch centrifugal ball mill, S1). The ground product was dried in a desiccator for 24 hours.

TABLE I

| Example No. | Surfactant | Amount of Surfactant (% w/w) | Amount of ethanol (or water) (g) |
|---|---|---|---|
| 1 | Lecithin | 1.0 | 1.2 |
| 2 | " | 0.2 | 1.2 |
| 3 | Sodium Lauryl Sulphate | 1.0 | 1.0 (water) |
| 4 | " | 0.1 | 1.0 (water) |
| 5 | Span 80 | 1.0 | 1.2 |
| 6 | " | 0.1 | 1.2 |
| 7 | Span 85 | 1.0 | 1.2 |
| 8 | " | 0.1 | 1.2 |
| 9 | Pluronic F68 | 1.0 | 1.2 |
| 10 | " | 0.1 | 1.2 |
| 11 | Sodium Docusate | 1.0 | 1.2 |
| 12 | " | 0.1 | 1.2 |
| 13 | DOPE | 1.0 | 1.2 |
| 14 | " | 0.1 | 1.2 |
| 15 | α-Glyceryl Monolaurate | 0.2 | 3.2 |
|  | Glyceryl Tripalmitate | 0.2 |  |
|  | Cholesterol | 0.2 |  |
|  | Cholesterol Acetate | 0.2 |  |
|  | Cholesterol Benzoate | 0.2 |  |
| 16 | α-Glyceryl Monolaurate | 0.02 | 1.2 |
|  | Glyceryl Tripalmitate | 0.02 |  |
|  | Cholesterol | 0.02 |  |
|  | Cholesterol Acetate | 0.02 |  |
|  | Cholesterol Benzoate | 0.02 |  |
| 17 | Hexadecanedioic Acid | 0.2 | 1.2 |
| 18 | Linolenic Acid | 1.0 | 1.2 |

EXAMPLES 19–22

The general procedure for Examples 1–18 was repeated except that the D-(+)-galactose was replaced by the carbohydrates listed in Table II, in the amounts and using the quantities of water shown, and that the surfactant used was palmitic acid (0.2% w/w relative to the carbohydrate) dissolved in 96% ethanol (1.2 g).

TABLE II

| Example No. | Microbubble-generating Carbohydrate | Amount of Carbohydrate (g) | Amount of water (g) |
|---|---|---|---|
| 19 | Xylose (BDH) | 10.0 | 14.2 |
| 20 | Maltodextrin | 10.0 | 14.2 |
| 21 | Glycogen (Merck) | 5.0 | 17.2 |
| 22 | α-Cyclodextrin (Sigma) | 5.0 | 12.2 |

EXAMPLE 23

6-O-Palmitoyl-D-galactopyranose/galactose Mixtures (A) 6-O-Palmitoyl-1,2,3,4-diisopropylidene-D-galactopyranose 1,2,3,4-Diisopropylidene-D-galactopyranose (Sigma, 13.4 g, 51.3 mmol) and triethylamine (7.15 ml, 51.3 mmol) were dissolved in methylene chloride (150 ml) and cooled to 0° C. Palmitoyl chloride (Aldrich, 14.1 g, 51.3 mmol) dissolved in methylene chloride (100 ml) was added dropwise with stirring over 1 h. The cooling bath was removed and the reaction mixture was stirred overnight. Precipitated triethylamine hydrochloride was removed by filtration, the filtrate was transferred to a separating funnel and extracted with water (3×50 ml), dried over $MgSO_4$ and the solvent was removed in vacuo. The residue was a light brownish oil which solidified to waxy crystals. Crude yield: 23 g. The crude product was used without further purification. A small aliquot was recrystallized for characterisation. FT-IR:CO-1734 $cm^{-1}$. $^{13}$C-NMR: CO-ester 172.79. Mp. 124°–127° C.

(B) 6-O-Palmitoyl-D-galactopyranose

6-O-Palmitoyl-1,2,3,4-diisopropylidene-D-galactopyranose (6 g) was dissolved in acetic acid (25 ml) and heated to 100° C. under nitrogen for 6h. During subsequent cooling to room temperature, the product precipitated from the solvent, and was left at room temperature overnight. The crystals were collected by filtration and dried under vacuum. Yield:3.3 g. The product was characterized by FT-IR:CO-1734 $cm^{-1}$; OH-3464 $cm^{-1}$.

(C) 6-O-Palmitoyl-D-galactopyranose/galactose Mixtures (i) D-(+)-galactose (2 g) was dissolved in purified water (2.87 g) and sterile filtered. 6-O-Palmitoyl-D-galactopyranose (0.25 g) prepared as described in (B) above was dissolved in ethanol (3 g) and sterile filtered. The solution of the palmitoyl-galactopyranose was added to the galactose solution under stirring and the whole mixture was taken to dryness under vacuum (10 torr, 50° C.). The product was dried in a desiccator overnight.

(ii) The procedure of (i) was repeated using 6-O-palmitoyl-D-galactopyranose (0.50 g) dissolved in ethanol (6 g).

EXAMPLE 24

Freeze-dried Liposomes Containing D-(+)-galactose Particles 1 ml 100 mg/ml phosphatidylcholine was dissolved in 10 ml chloroform. The mixture was poured into a round bottom flask, and the organic phase was evaporated at 40° C. in such a way that a thin film of the phosphatidylcholine was formed on the inner surface of the flask. 10 ml of a sterile, pyrogen free 40% aqueous D-(+)-galactose solution was then added at 40° C. and the flask was kept rotating for 1 hour. The aqueous solution containing liposomes and dissolved galactose was then freeze-dried for 24 hours, and the resulting product consisting of freeze-dried galactose and freeze-dried galactose-filled liposomes was then ground in a ball-mill to yield a product with a particle size distribution of 1–20 μm.

EXAMPLE 25

Echogenicity in Vitro 10 ml of propylene glycol mixed with 90 ml of 5% dextrose in water was used as a carrier liquid for determining the echogenicity of products according to the Examples. 1.0 g of each product to be tested was dispersed in 3.0 ml of the carrier liquid and shaken for 15 seconds. The resulting mixture was added to 52 ml of 5% human serum albumin infusion solution in the measurement cell and the acoustic effects of the products were investigated by measuring the acoustic transmission through the samples using a 5 MHz broadband transducer in a pulse-reflection technique. The temperature in the measurement cell was stabilised to 37° C.

and circulation of the liquid was maintained by means of stirring at a constant rate. Ultrasound transmission through the samples was measured as a function of time over a duration of 390 seconds. Results were normalized to measurements on a reference consisting of 55 ml of 5% human serum albumin infusion solution.

Results for representative exemplified products and comparative results for unmodified milled D-(+)-galactose are shown in the accompanying drawing as FIG. 1. It will be apparent that these products exhibit a strong effect on ultrasonic attenuation in vitro, an effect which persisted for several minutes.

We claim:

1. A contrast agent comprising gas microbubble-generating microparticles comprising a carbohydrate and admixed within the microparticulate structure a surfactant, the microbubbles generated by said microparticles comprising a biocompatible low molecular weight fluorinated hydrocarbon.

2. A contrast agent as claimed in claim 1 in which the carbohydrate is selected from the group consisting of water-soluble pentoses, hexoses, disaccharides, polysaccharides and sugar alcohols.

3. A contrast agent as claimed in claim 2 in which the carbohydrate is galactose.

4. A contrast agent as claimed in claim 1 in which the surfactant is selected from the group consisting of: straight chain aliphatic carboxylic acids and salts, sorbitan esters and mono- and di-glycerides thereof; aralkanoic acids and salts thereof; steroid acids; sterols; straight chain aliphatic alcohols; phospholipids; alkali metal alkyl sulphates and sulphonated esters; polyoxyethylene-polyoxypropylene copolymers; polyoxyethylated sorbitan esters; and mixtures of any of the foregoing.

5. A contrast agent as claimed in claim 1 in which the surfactant comprises a lipophilically modified carbohydrate.

6. A contrast agent as claimed in claim 1 in which the surfactant is present in an amount of 0.1–2.0% w/w relative to the carbohydrate.

7. A contrast agent as claimed in claim 1 in which the microparticles are aggregates having an aggregate size of 30–50 micrometers of microparticles having a particle size of 1–10 micrometers.

8. A contrast agent as claimed in claim 1, for which the microbubbles generated by said microparticles contain air in admixture with said fluorinated hydrocarbon.

9. A contrast agent as claimed in claim 1 for which the microbubbles generated by said microparticles comprise carbon tetrafluoride.

10. A contrast agent as claimed in claim 1 in which the carbohydrate is a water-soluble polysaccharide.

11. A contrast agent as claimed in claim 2 in which the surfactant is selected from the group consisting of phospholipids, polyoxyethylene-polyoxypropylene copolymers and mixtures thereof.

12. A contrast agent as claimed in claim 1 which is non-contrast giving before use, but which becomes effective on administration.

13. A contrast agent as claimed in claim 2 which is non-contrast giving before use, but which becomes effective on administration.

14. A contrast agent as claimed in claim 3 which is non-contrast giving before use, but which becomes effective on administration.

15. A contrast agent as claimed in claim 4 which is non-contrast giving before use, but which becomes effective on administration.

16. A contrast agent as claimed in claim 5 which is non-contrast giving before use, but which becomes effective on administration.

17. A contrast agent as claimed in claim 6 which is non-contrast giving before use, but which becomes effective on administration.

18. A contrast agent as claimed in claim 7 which is non-contrast giving before use, but which becomes effective on administration.

19. A contrast agent as claimed in claim 8 which is non-contrast giving before use, but which becomes effective on administration.

20. A contrast agent as claimed in claim 9 which is non-contrast giving before use, but which becomes effective on administration.

21. A contrast agent as claimed in claim 10 which is non-contrast giving before use, but which becomes effective on administration.

22. A contrast agent as claimed in claim 11 which is non-contrast giving before use, but which becomes effective on administration.

23. A contrast agent as claimed in claim 1 which on formulation for administration generates gas microbubbles on dissolution of the carbohydrate.

24. A contrast agent as claimed in claim 2 which on formulation for administration generates gas microbubbles on dissolution of the carbohydrate.

25. A contrast agent as claimed in claim 3 which on formulation for administration generates gas microbubbles on dissolution of the carbohydrate.

26. A contrast agent as claimed in claim 4 which on formulation for administration generates gas microbubbles on dissolution of the carbohydrate.

27. A contrast agent as claimed in claim 5 which on formulation for administration generates gas microbubbles on dissolution of the carbohydrate.

28. A contrast agent as claimed in claim 6 which on formulation for administration generates gas microbubbles on dissolution of the carbohydrate.

29. A contrast agent as claimed in claim 7 which on formulation for administration generates gas microbubbles on dissolution of the carbohydrate.

30. A contrast agent as claimed in claim 8 which on formulation for administration generates gas microbubbles on dissolution of the carbohydrate.

31. A contrast agent as claimed in claim 9 which on formulation for administration generates gas microbubbles on dissolution of the carbohydrate.

32. A contrast agent as claimed in claim 10 which on formulation for administration generates gas microbubbles on dissolution of the carbohydrate.

33. A contrast agent as claimed in claim 11 which on formulation for administration generates gas microbubbles on dissolution of the carbohydrate.

34. A process for preparing a contrast agent as claimed in claim 1 which comprises (i) either mixing solutions of the carbohydrate and surfactant and removing the solvent(s) therefrom or mixing a solution of the carbohydrate with a liposome-forming material and removing the solvent therefrom and (ii) micronising the resulting mixture to yield the desired microparticles.

35. A process as claimed in claim 34 in which the mixture is micronised by ball-milling.

36. A method of generating an enhanced diagnostic image of a human or non-human animal body comprising administering into the vascular system of said body a diagnostic image enhancing amount of a contrast agent according to claim 1.

37. A method of generating an enhanced diagnostic ultrasonic image of a human or non-human animal body comprising administering into the vascular system of said body a diagnostic ultrasonic image enhancing amount of a contrast agent according to claim 1.

38. A method of generating an enhanced magnetic resonance image of a human or non-human animal body comprising administering to said body a magnetic resonance image enhancing amount of a contrast agent according to claim 1.

* * * * *